United States Patent
Ramsteiner

(10) Patent No.: US 9,439,588 B2
(45) Date of Patent: Sep. 13, 2016

(54) ARRANGEMENT AND DEVICES CONFIGURED FOR CARRYING OUT OPTICAL ABSORPTION SPECTROSCOPY

(71) Applicant: Robert Bosch GmbH, Stuttgart (DE)

(72) Inventor: Ingo Ramsteiner, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 250 days.

(21) Appl. No.: 14/154,978

(22) Filed: Jan. 14, 2014

(65) Prior Publication Data
US 2014/0213860 A1 Jul. 31, 2014

(30) Foreign Application Priority Data

Jan. 28, 2013 (DE) .................. 10 2013 201 275

(51) Int. Cl.
*A61B 5/1455* (2006.01)
*A61B 5/1459* (2006.01)
*A61B 5/00* (2006.01)

(52) U.S. Cl.
CPC ........... *A61B 5/1459* (2013.01); *A61B 5/0059* (2013.01); *A61B 5/0071* (2013.01); *A61B 5/0075* (2013.01); *A61B 5/441* (2013.01); *A61B 5/686* (2013.01); *A61B 5/6867* (2013.01)

(58) Field of Classification Search
CPC .. A61B 5/1455; A61B 5/1459; A61B 5/686; A61B 5/0059; A61B 5/0071
See application file for complete search history.

(56) References Cited

U.S. PATENT DOCUMENTS

| | | | |
|---|---|---|---|
| 5,143,066 A | 9/1992 | Komives et al. | |
| 5,342,789 A * | 8/1994 | Chick | A61K 49/0004 600/322 |
| 6,256,522 B1 | 7/2001 | Schultz | |
| 6,766,183 B2 * | 7/2004 | Walsh | A61B 5/1455 600/341 |
| 2006/0224056 A1* | 10/2006 | Kermani | A61B 5/14532 600/317 |
| 2011/0224514 A1 | 9/2011 | Müller et al. | |

FOREIGN PATENT DOCUMENTS

DE 10 2010 001 220 A1 7/2011
WO 01/26540 A1 4/2001

* cited by examiner

*Primary Examiner* — Eric Winakur
(74) *Attorney, Agent, or Firm* — Maginot, Moore & Beck LLP

(57) ABSTRACT

An implantable fluorescent concentrator is configured to be inserted in vivo as a subcutaneous light source for optical absorption spectroscopy of surface-near tissue layers. As a result, certain and reliable results of the optical absorption spectroscopy are achievable. Furthermore, various analytes with different absorption properties are certainly and reliably quantifiable.

15 Claims, 4 Drawing Sheets

ARRANGEMENT AND DEVICES CONFIGURED FOR CARRYING OUT OPTICAL ABSORPTION SPECTROSCOPY

This application claims priority under 35 U.S.C. §119 to patent application number DE 10 2013 201 275.6, filed on Jan. 28, 2013 in Germany, the disclosure of which is incorporated herein by reference in its entirety.

BACKGROUND

The disclosure relates to an arrangement having devices that permit optical absorption spectroscopy to be carried out.

The absorption spectrum of living tissue, in particular skin, has relatively low light absorption over wide ranges and is therefore generally accessible to spectroscopy with corresponding light wavelengths. One technical difficulty here is the strong scattering of the light in tissue. Depending on the wavelength, the light can travel distances of a few centimeters in the tissue, but covers such distances only via numerous scattering processes. The propagation of light in the tissue corresponds to a diffusion process rather than to the light propagation of straight-line rays. Owing to this uncertainty relating to the optical paths in the tissue, carrying out spectroscopy in the tissue becomes more difficult. The resulting results may be falsified in the process. It might also be the case that weakly absorbing particles (for example molecules, ions, electrons) as analytes in very small concentrations can be quantified with difficulty or hardly at all. Glucose, for example, is such a weakly absorbing molecule.

There is thus a continued need for improved procedures and devices for carrying out optical absorption spectroscopy. It is desirable, for example, to reliably quantify different analytes independently of their absorption strength despite the strong scattering of the light in the tissue.

SUMMARY

The present disclosure is essentially specified by the features described below. Further configurations of the present disclosure can be gathered by way of example from the below description.

The idea of the present disclosure is to place the light source that is necessary for carrying out the absorption spectroscopy under the skin surface in the manner of an implant. Such a light source should as far as possible be a point-type light source and emit light only in the direction of the detector detecting the light from the light source. The present disclosure in this case realizes the light source as a fluorescent concentrator. Here, a fluorescent dye is applied onto a transparent plate or is embedded into the material of the plate. Light that is incident through the skin surface excites the dye to isotropically emitted fluorescence. Since the emission takes place within the material, a majority of the light remains trapped inside the plate due to total internal reflection, as in the case of an optical waveguide, and can be coupled out as far as possible in a point-type fashion at a location that is intended therefor. On account of the fact that the light source according to the disclosure is realized in the form of a fluorescent concentrator, the light source can concentrate diffuse light, as is present also in the tissue after emission through the skin surface. The fluorescent concentrator captures the light that is incident into the tissue with its entire surface, converts it into fluorescent light having a greater wavelength, and emits it from approximately a point in the direction of the detector at the skin surface. Once detected, the emitted fluorescent light can be evaluated using the known methods of absorption spectroscopy.

Despite the strong scattering of the light in the tissue, the present disclosure makes it possible for various analytes to be reliably quantified independently of their absorption strength. Furthermore, the results of the absorption spectroscopy are reliable because the present disclosure is able to collect and concentrate the light that is scattered diffusely within the tissue well and emit the light required for the absorption spectroscopy with greater wavelengths in the direction of the skin surface. The wavelengths of the light emitted by the light source according to the disclosure are greater than those of the light that is absorbed by the light source according to the disclosure. In addition, no energy supply for the light source is necessary for carrying out the absorption spectroscopy.

BRIEF DESCRIPTION OF THE DRAWINGS

The following figures schematically describe the disclosure in more detail with respect to embodiments. For the sake of clarity, identical or identically acting elements may have the same reference signs.

DETAILED DESCRIPTION

Figure 1:
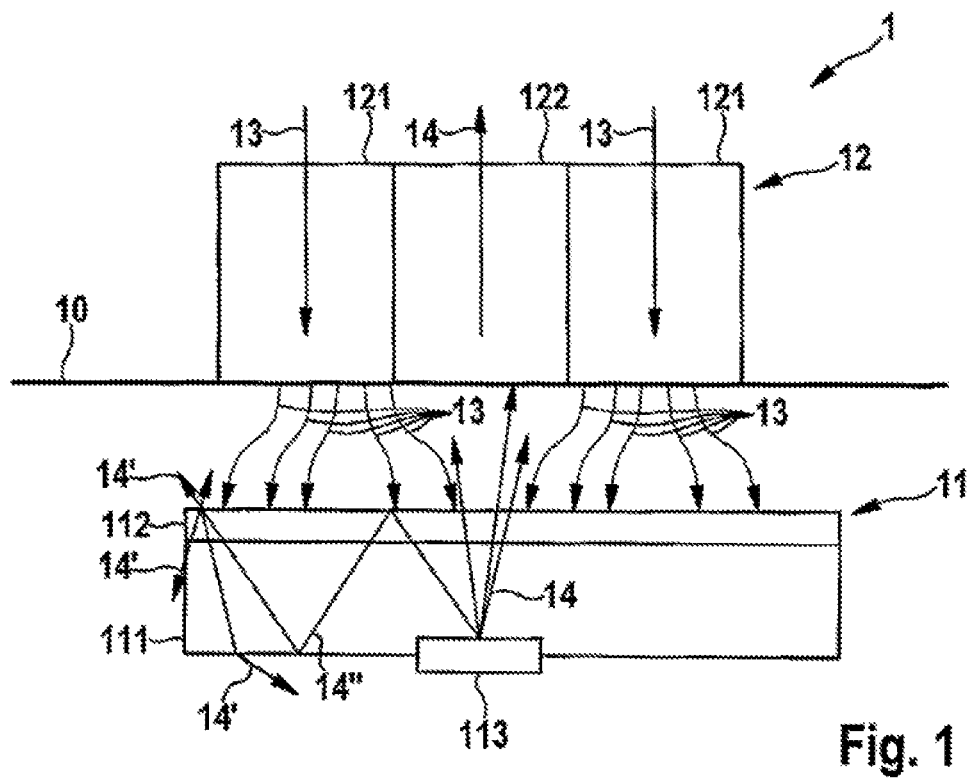
FIG. 1 shows an arrangement according to one embodiment of the present disclosure.

FIG. 1 shows an arrangement 1 according to one embodiment of the present disclosure. The arrangement 1 has, according to the present embodiment, a device 11 (as the abovementioned light source), which: is configured to be inserted under a skin surface 10; has a fluorescent layer 112, wherein the fluorescent layer 112 is configured to absorb light 13 that is emitted onto the skin surface 10 and to convert the absorbed light into fluorescent light; has a fluorescent-light-emitting region 113 which is configured to absorb the fluorescent light and to emit it in the direction of the skin surface 10 (see the arrows having the reference sign 14). The fluorescent layer 112 can, for example, be formed on a side of the device 11 facing the skin surface 10. According to the present embodiment, the device 11 furthermore has a substrate 111. The fluorescent layer 112 can be formed for example on the substrate 111. The fluorescent light absorbed in the substrate 111 (see reference sign 14") and supplied to the fluorescent-light-emitting region 113. The region 113, which emits the fluorescent light 14", 14, couples out the fluorescent light 14", 14 absorbed in the device 11 and emits it in the direction of the skin surface 10. Since the device 11 is inserted under the skin surface 10, it may also be referred to as an implant. The examination of the tissue, of the fluids, and/or of the particles located between the device 11 and the skin surface 10 is made possible and improved by the device 11. As already mentioned, the problem of strong scattering of the light under the skin surface 10 frequently occurs in the case of examinations using light, which makes spectroscopy of the tissue, of the fluids, and/or of the particles more difficult. According to the present disclosure, a large portion of the light scattered under the skin surface 10 is absorbed by the device 11, so that the portion of the light which is scattered under the skin surface 10 in another way remains small and can no longer negatively influence the result of the spectroscopy. Owing to total internal reflection in the device 11 (for example in its plate or in the substrate 111), the absorbed light remains trapped as fluorescent light in the device 11, in the manner of an optical waveguide, and is coupled out only at the location of the device 11 that is intended therefor—in the fluorescent-light-emitting region 113—and is emitted in the direction of the skin surface 10. The present disclosure realizes the device 11 as a fluorescent concentrator, which can concentrate diffuse light. The fluorescent light emitted by the device 11 (that is to say by the fluorescent-light-emitting region 113) in the direction of the skin surface 10 can be differentiated easily from the light 14' emitted through the skin surface 10 in another way, which considerably increases and improves the reliability of the results of the spectroscopy. The light 14' emitted through the skin surface 10 in another way can comprise light that is emitted by the device 11 in another way, that is to say is not emitted by the region 113 and/or emitted otherwise by the tissue. For evaluating the fluorescent light emitted by the device 11, various known methods of absorption spectroscopy can be used, for example. Furthermore, no energy supply is necessary for the device 11 with the present disclosure. The device 11 can moreover remain (as an implant) in the body or under the skin surface 10 generally unlimited time period, as a result of which the examinations of the tissue, the fluids, and/or the particles can be repeated at any time and as a result of which the examinations can be carried out simply and without further actions.

For irradiating the skin surface 10 and thus for supplying the light 13 to the device 11 through the skin surface 10, the arrangement 1 according to the present embodiment has a light-detecting device 12. According to the present embodiment, the light-detecting device 12 is configured to emit light 13 onto the skin surface 10 and to receive the fluorescent light 14 which was emitted by the device 11 according to the disclosure. The fluorescent light 14 that was emitted by the device 11 according to the disclosure is used by the light-detecting device 12 to evaluate the emitted fluorescent light 14. The device 11 only emits the fluorescent light 14 after the light 13 is emitted onto the skin surface 10. According to the present embodiment, this therefore occurs in response to the emission of the light 13 by the light-detecting device 12.

According to the present embodiment, the light-detecting device 12 has at least one light-emitting element 121, which is configured to emit light 13 onto the skin surface 10. The light-detecting device 12 furthermore has at least one light-receiving element 122, which is configured to detect and to receive the fluorescent light 14 which was emitted by the device 11 (that is to say by the region 113 thereof intended therefor). The light-detecting device 12 can, after it receives the fluorescent light 14, evaluate it or provide it to a further device intended therefor for evaluation. The light-detecting device 12 can be a probe, for example. The at least one light-emitting element 121 can be, for example, an optical fiber configured for lighting. The at least one light-receiving element 122 can be, for example, an optical fiber configured for detecting the received fluorescent light 14.

FIG. 1 shows the device 11 in a state in which it is inserted or implanted under the skin surface 10. The exact depth or thickness of the skin layer depends on the field of use of the arrangement 1 with the two devices 11 and 12. The tissue to be examined spectroscopically is located between the device 11 (for example the implant 11) and the light-detecting device 12 (for example a probe 12) disposed on the skin surface 10. Using the light-detecting device 12, light 13 (also referred to as excitation light below) is irradiated into the skin 10 and spreads diffusely in the tissue. The device 11 collects (using the fluorescent layer 112) a large portion of the light 13 irradiated into the skin 10, converts it (using the fluorescent layer) into the fluorescent light 14', and radiates the obtained fluorescent light 14', 14 in the direction of the light-detecting device 12.

The device 11 can have a flat-surface configuration, as a result of which the device 11 obtains an improved property of light absorption, i.e. the device 11 can collect or absorb more of the light 13 that is emitted onto the skin surface 10 and distributed in the tissue.

The fluorescent-light-emitting region 113 can be smaller than the side of the device 11 facing the skin surface. In this case, the fluorescent-light-emitting region 113 is smaller than the fluorescent layer 112. As a result, the fluorescent light 14 which is emitted by the device 11 (or by the region 113) according to the disclosure can be differentiated better from the light 14' which is emitted in another way through the skin surface 10. The fluorescent-light-emitting region 113 can be configured here such that it constitutes, viewed from the light-detecting device 12, a nearly point-type light source arranged in the tissue, which light source can be used for absorption spectroscopy of the tissue located between the two devices 11 and 12, the fluids located between the two devices 11 and 12, and/or the particles located between the two devices 11 and 12. In this manner, the light 14', which is trapped in the device 11, is coupled out and emitted in a point-type fashion through the region 113 (see arrows 14). The absorption spectroscopy of the fluorescent light 14 emitted according to the disclosure can then be carried out by the light-detecting device 12 or another suitable device using methods known therefor.

Figure 2:
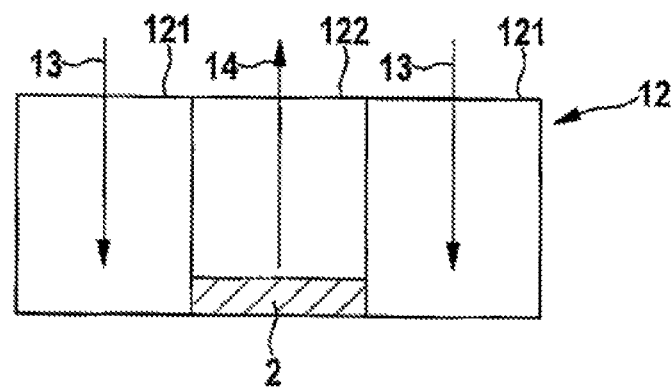
FIG. 2 shows a light-detecting device according to one embodiment of the present disclosure.

According to the present embodiment, the wavelength of the emitted (by the fluorescent-light-emitting region 113) fluorescent light 14 is greater than the wavelength of the absorbed (by the fluorescent layer 112) light 13. Here, the absorption and emission bands of the fluorescent agent used for the fluorescent layer 112 overlap spectrally only partially and preferably not at all. In this manner, the fluorescent light 14 emitted by the device 11 according to the disclosure and the light 14' scattered back in another way by the tissue and by the device 11 can be differentiated well using known methods of spectroscopy. The light-detecting device 12 can have a filter element 2, which transmits the fluorescent light 14 emitted by the device 11 for evaluation by the light-detecting device 12 and blocks other light 14' emitted by the skin surface 10. An exemplary embodiment of the light-detecting device 12 with the filter element 2 is shown in FIG. 2. The filter element 2 can be arranged on the side of the light-detecting device 12 which is aligned with the skin surface 10, in front of the light-receiving element 122. The filter element 2 can be, for example, a spectral edge filter, which blocks light having wavelengths below the fluorescence band of the device 11. Use of the filter element 2, which is made possible by the differentiability of the fluorescent light 14 emitted by the device 11 (or by the region 113), explained above, ensures that only the light that is indeed to be examined is used for the evaluation using spectroscopy, in particular using absorption spectroscopy. Thus the significance, certitude, reliability of the evaluated values are increased. Overall, the examination of the tissue, of the fluids, and/or of the particles between the skin surface 10 and the device 11 becomes more precise and simple.

Figure 3:
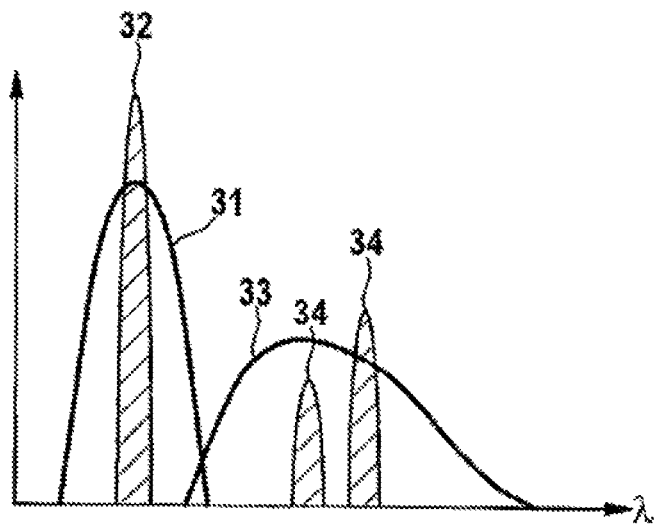
FIG. 3 shows the spectral relationships between the light that is absorbed by the fluorescent layer and the fluorescent light emitted according to one embodiment of the present disclosure.

FIG. 3 shows the spectral relationships between the light absorbed by the fluorescent layer 112 and the fluorescent light 14 emitted according to one embodiment of the present disclosure. The horizontal axis here shows the wavelength $\lambda$ in nm, and the vertical axis indicates the strength of absorption or emission, wherein the wavelength $\lambda$ is given on the horizontal axis in an ascending order (from left to right). According to FIG. 2, the fluorescent layer 112 absorbs the light 13 irradiated through the skin surface 10 in a region 31 which covers the region 32 of the light 13 emitted by the light-detecting device 12. The fluorescent light 14 is emitted according to the present embodiment in a region 33 which is different or separate from the absorption region 31 and comprises the characteristic absorption bands 34 of the analyte (that is to say of the tissue to be examined, of the fluid to be examined, and/or of the particles to be examined).

Figure 4:
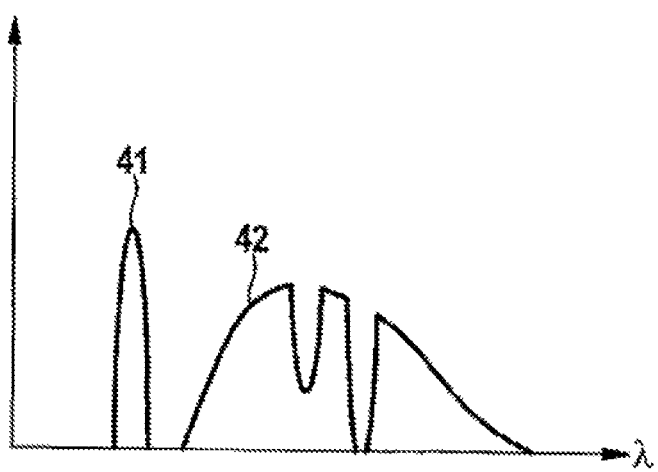
FIG. 4 shows the spectral relationships between light which is scattered back in another way after irradiation with the light from a light-detecting device and the emitted fluorescent light according to one embodiment of the present disclosure.

FIG. 4 shows the spectral relationships between the light which is radiated back in another way (for example 14' in FIG. 1), which was radiated back after irradiation using the light 13 from the light-detecting device 12, and the fluorescent light 14 emitted by the device 11 (or by the region 113) according to one embodiment of the present disclosure. The emitted fluorescent light 14 is here locally attenuated by the absorption by the analyte (that is to say of the tissue to be examined, the fluid to be examined, and/or the particles to be examined). In FIG. 4, the region 41 belongs to the other light which is radiated back (for example 14' in FIG. 1), and region 42 belongs to the emitted fluorescent light 14, which is locally attenuated owing to the absorption by the analyte. In region 42, the fluorescent signal with absorption lines of the analyte is shown. The axes in FIG. 4 correspond to the axes in FIG. 3.

According to one embodiment of the present disclosure, the device 11 or the substrate 111 of the device 11 is made of a high-refractive (high-n) material. The refractive index of the material of the device 11 or of the substrate 111 is preferably greater than the refractive index of the surrounding biomaterial or of the surrounding tissue, respectively. This supports the differentiability between the fluorescent light 14 emitted by the device 11 and the other light 14' emitted via the skin surface 10, since the total internal reflection occurs owing to media at the boundary surfaces to high-refractive media, that is to say in this case at the boundary surfaces from the tissue to the device 11 or to the substrate 111 of the device 11, respectively. In this manner, the reliability of the results of the spectroscopy and in particular of the absorption spectroscopy during examination of the emitted fluorescent light 14 is increased. If, for example, the refractive index n for the tissue-fluid is given as n=1.36, this could have the following refractive indices for the device 11 or for the substrate 111 for example for the following used materials: for glass, the refractive index n=1.52, for plastic such as for example polymethyl methacrylate (PMMA) the refractive index n=1.49, for plastic such as polystyrene the refractive index n=1.58. It should be noted here that the above specifications of the materials and the associated refractive indices are merely exemplary and that the present disclosure permits use of other suitable materials and/or other suitable refractive indices. In principle, the refractive index of the device 11 or of the substrate 111 should be as large as possible, in any case greater than the refractive index of the biological material (of the tissue) surrounding the device 11.

According to one embodiment of the present disclosure, the fluorescent layer 112 has a refractive index which is comparable with the refractive index of the device 11 or of the substrate 111, for example is the same or approximately the same. As a result, Fresnel reflections at the boundary surface between the materials of the layer 112 and of the substrate 111 are minimized and unobstructed conduction of the light 14" to the coupling-out location 113 is ensured.

The fluorescent layer 112 can be one of the layers configured as follows: a layer made of a fluorescent dye or a layer configured from the material of the substrate 111 or the device 11 and from a fluorescent dye, wherein the fluorescent dye is embedded in the material of the substrate 111 or of the device 11. The present disclosure permits certain flexibility in relation to the configuration of the fluorescent layer 112. The above-mentioned possible configurations of the fluorescent layer 112 support the property of differentiability of the fluorescent light 14 emitted by the device 11 (or by the fluorescent-light-emitting region 113) and the light 14' emitted in another way. Furthermore, the reliability of the results obtained after evaluation of the emitted fluorescent light 14 is increased. If, for example, the material of the substrate 111 or of the device 11 is PMMA, the PMMA can be dyed using a fluorescent dye to form the fluorescent layer 112. In such a case, a separation of substrate 111 and fluorescent layer 112 is no longer absolutely necessary—instead, the substrate 111 can also be dyed homogeneously with the fluorescent dye, and a fluorescent layer 112 which can be differentiated from the substrate can be omitted entirely. Therefore, the present disclosure permits an embodiment with a layer (with 111 and 112) in which the substrate 111 and the fluorescent layer 112 are connected or combined by dying or introducing the fluorescent dye in the material of the substrate 111. The present specification deals with both layers—the substrate 111 and the fluorescent layer 112—separately for reasons of clear and concise illustration, but also comprises the embodiment with just one layer connecting or combining the layers 111 and 112. Here, the features, advantages, functions and further configurations of the substrate 111 and of the fluorescent layer 112 are also accordingly comprised by the one layer comprising both layers 111, 112.

The absorption and emission bands of the fluorescent agent or of the fluorescent dye overlap spectrally only partially or not at all, as a result of which the above-mentioned properties of differentiability of the emitted fluorescent light 14 from the otherwise emitted light 14' and reliability of the results of the evaluation of the emitted fluorescent light 14 are likewise ensured and supported. For example, the fluorescent agent or the fluorescent dye can absorb the light 13 emitted onto the skin surface only in a limited spectral range and emit it by way of fluorescence with high quantum efficiency (for example greater than 90%) in a likewise limited spectral range separate from the absorption band. The fluorescent agent or the fluorescent dye can be, for example, a laser dye, a neon color (for example for highlighters) or a substance based on organic dyes such as perylene or naphthalimide. Alternatively, quantum dots can be used to form the fluorescent layer.

Generally, the choice of fluorescent agent or of fluorescent dye should be made in correspondence with the respective use. In order to support and to ensure the positive effects of the present disclosure, the absorption band of the fluorescent agent or of the fluorescent dye should include the wavelength of the light 13 irradiated through the skin surface 10. The emission band of the fluorescent agent or of the fluorescent dye should include the wavelengths required for spectroscopy. For example, the emission should be configured to have as broad a band as possible and include one or more characteristic absorption bands of the analyte to be measured (completely or nearly completely or as completely as possible).

According to one embodiment of the present disclosure, the fluorescent-light-emitting region 113 is one of the regions configured as follows: a roughened region, and/or a region covered with scattering particles, of a surface of the substrate 111 or of the device 11 that extends with the skin surface, or a light-scattering region in the volume of the substrate 111 or of the device 11. The regions 113, which are configured in this way and emit the fluorescent light, permit a point-type emission or a nearly point-type emission of the fluorescent light 14, as a result of which the above-mentioned properties of differentiability of the fluorescent light 14 emitted by the device 11 (or by the fluorescent-light-emitting region 113) and of the light 14' emitted in another way. Furthermore, the reliability of the results obtained after evaluation of the emitted fluorescent light 14 is increased.

The above-mentioned positive effects (differentiability, reliability) of the roughened region 113 and/or the region 113 covered with scattering particles is based on a disturbance of the total internal reflection in the region 113. The positive effect is amplified according to one embodiment by the fact that the device 11 or the substrate 111 has a reflector at a side of the fluorescent-light-emitting region 113 facing away from the skin surface 10 and/or that the fluorescent-light-emitting region 113 is formed on a surface of the substrate 111 or of the device 11 facing away from the skin surface 10. The reflector is used to additionally direct the scattered light in the direction of the skin surface 10.

If the fluorescent-light-emitting region 113 is a light-scattering region in the volume of the substrate 111 or of the device 11, it may be formed for example by microscopically small air inclusions or microcracks in the substrate 111 or in the device 11. If, for example, glass is the material used for the substrate 111 or the device 11, microscopically small air inclusions or microcracks in the substrate 111 or in the device 11 can be formed by using internal laser engraving. If, for example, plastic is used as the material for the substrate 111 or the device 11, the fluorescent-light-emitting region 113 can be formed by embedding a scatter body in the volume of the substrate 111 or of the device 11.

Figure 5:
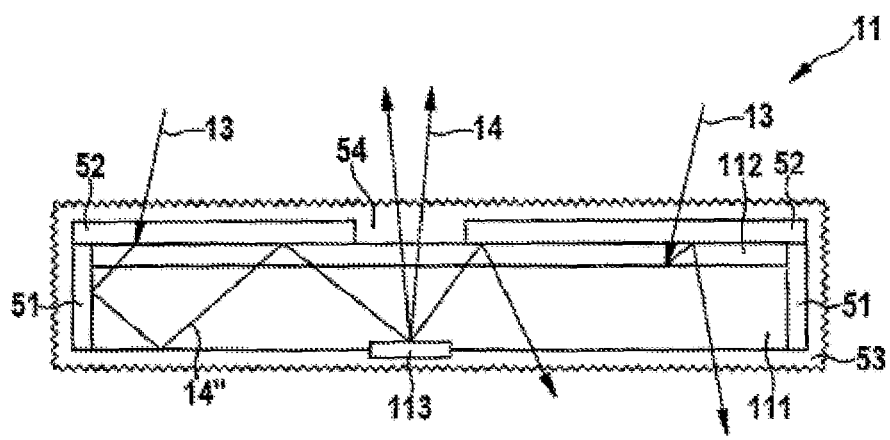
FIG. 5 shows a configuration of the device according to one embodiment of the present disclosure that is insertable under the skin surface.

FIG. 5 shows an embodiment of the device 11 which is insertable under the skin surface according to one further embodiment of the present disclosure. It should be noted here that each of the further components of the device 11 shown in FIG. 5 can be used alone and/or in combination with at least one further one of the components shown in FIG. 5 for configuring the device 11. FIG. 5 shows the device 11 with all further components which are possible according to the present disclosure, so as to keep the description short and clear.

According to the present embodiment, the device 11 has a mirror 51 at least at one front end of the device 11 or at least at one edge face of the device 11, respectively, wherein the at least one mirror 51 is configured to reflect fluorescent light 14" propagating within the layer 112 or substrate 111, which fluorescent light 14" would otherwise exit the device 11 at the relevant edge or front end since it does not meet the prerequisites for total internal reflection. The front end or the edge face of the device 11 is the side or face of the device that does not extend (substantially parallel) with the skin surface 10. Rather, it extends counter to the skin surface 10, for example substantially perpendicular with respect to the skin surface 10. The device 11 has at least one mirror 51. Light rays 13, 14" that extend at flat angles with respect to the plane of the device 11 or of the substrate 111, and are therefore reflected totally at the upper or lower side of the device 11, strike the edge face under relatively steep angles and can be coupled out there. This can be prevented by making these surfaces reflective (for example a metallic, preferably silver or gold reflective coating). In this way, the light 14", which is trapped in the device 11, is prevented from radiating out. As a result, the amount of the other light 14' emitted by the tissue is reduced, which ultimately results in better differentiability between the light 14 emitted by the device 11 (or by the fluorescent-light-emitting region 113) and the other light 14' emitted from the tissue and entails better results for the evaluation of the emitted fluorescent light 14.

According to the present embodiment, the device 11 has, on that side of the device 11 which faces the skin surface, a fluorescent-light-controlling layer 52. The fluorescent-light-controlling layer 52 is formed over the fluorescent layer 112. Here, the fluorescent-light-controlling layer 52 is substantially transparent for the light 13 emitted onto the skin surface 10 and substantially reflective or absorbing for the emitted fluorescent light 14. The fluorescent-light-controlling layer is configured to direct the emission of the fluorescent light 14 to a specific position on the skin surface 10.

According to the present embodiment, the fluorescent-light-controlling layer 52 is open with respect to the fluorescent-light-emitting region 113 (see opening 54 in FIG. 5) such that the fluorescent light 14 emitting from the fluorescent-light-emitting region 113 is emitted to the specific position on the skin surface 10. Here, the fluorescent light 14 is emitted through the opening 54 of the fluorescent-light-controlling layer 52 in the direction of the skin surface 10. Even though the light is coupled out according to the present disclosure mainly at the scatter zone or in the fluorescent-light-emitting region 113, since the fluorescent light 14 is emitted isotropically, the coupled-out light is, however, not completely subject to total internal reflection. With a correspondingly steep angle with respect to the boundary surface between the device 11 and the surrounding area of the device 11, light rays of the fluorescent light 14" produced by the fluorescent layer can exit the device 11. Scattering at usually unavoidable material defects can also result in undesired coupling out of the fluorescent light 14" produced by the fluorescent layer. With the use of the fluorescent-light-controlling layer 52, the emission of the produced fluorescent light 14 can be achieved completely at the location intended therefor or on the fluorescent-light-emitting region 113. According to the present embodiment, the fluorescent-light-controlling layer 52 is located between the fluorescent layer 112 and the skin surface 10, for example on the fluorescent layer 112. If the device 11 is surrounded by an encapsulation material, which will be explained in more detail below, the fluorescent-light-controlling layer 52 can also be formed on its surface. The fluorescent-light-controlling layer 52 is open above the fluorescent-light-emitting region 113 (see opening 54). Moreover, the divergence of the emitted fluorescent light 14 can be set by way of the relationship of the radii of the opening 54 of the fluorescent-light-controlling layer 52 and of the fluorescent-light-emitting region 113.

The fluorescent-light-controlling layer 52 can be formed for example by dielectric interference filters. By way of a targeted configuration of a sequence of dielectric layers with varying refractive indices, it is possible to set the reflection and transmission behavior of such layer systems virtually as desired. The relevant high low or bandpass filters are available and usable for all spectral ranges.

Furthermore, the fluorescent-light-controlling layer 52 can be formed for example by transparent conductive layers. Here, the fluorescent-light-controlling layer 52 can be formed for example from transparent conductive metal oxides (TCO materials), such as for example variously doped indium zinc or zinc oxides. These have the property of transparency, exhibit good transmission properties in the visible spectral range, and at the same time are good reflectors in the near infrared. The plasma frequency is then important for the position of the reflection edge.

Moreover, the fluorescent-light-controlling layer 52 can be formed using dye systems. To this end, any dye (organic, inorganic or quantum dots), whose absorption band includes the emission band of the fluorescent dye used in the implant but not the wavelength of the excitation light, is suitable. The dye should furthermore return into its ground state without radiation after irradiation via the skin surface 10 or emitted in a spectral range irrelevant for the spectroscopy, wherein this spectral range does not overlap with the emission spectral range of the fluorescent light 14 emitted by the device 11 (or by the fluorescent-light-emitting region 113). The above-described fluorescent-light-controlling layer 52 can also be referred to as a spectrally selective layer (SSS).

According to the present embodiment, the device 11 is encapsulated or overmolded in a low-n material 53. It is difficult to configure a component consisting of various materials to be biocompatible. This, however, should be done with respect to the device 11, since the device 11 is intended for implantation under the skin surface 10 and should therefore be biocompatible. That is to say, the organism and its tissue must not be damaged by the device 11. Furthermore, the upper and boundary surface quality which is decisive for the optical functionality can hardly be maintained for a longer period of time. For example, a living organism will damage most foreign bodies electromechanically within a short period of time or at least cover it with a protein film. Both influence the boundary surface reflections. One solution to this problem is to encapsulate the device 11 in a material 53 which causes no physiological damage and is resistant to biochemical attacks. Crucial for the optics is the quality of the protected internal boundary surfaces. The quality of the encapsulation surface is irrelevant and can certainly be rough, since the surrounding area of the device 11 (that is to say the tissue) already has a very strongly scattering effect. The refractive index of the encapsulation material 53 should be as close as possible to the refractive index of the surrounding tissue so as to minimize the optical action of the boundary surface. If this is not possible, the refractive index of the encapsulation material 53 should preferably be smaller than that of the surrounding tissue.

According to a further embodiment of the present disclosure, it is possible to select, instead of the fluorescent-light-controlling layer 52 or the spectrally selective layer (SSS) 52, an encapsulation material 53 which absorbs the fluorescent light 14. That is to say, with a suitable encapsulation material 53, the configuration of the device 11 with the fluorescent-light-controlling layer 52 may also be omitted. In this case, transparency must nevertheless be produced at or over the fluorescent-light-emitting region 113. This can be achieved for example by way of a locally thinner encapsulation layer or an encapsulation layer of different composition over the fluorescent-light-emitting region 113. This encapsulation layer which is configured differently locally would be arranged at the same position as the location of the opening 54 in the fluorescent-light-controlling layer 52.

Figure 6:
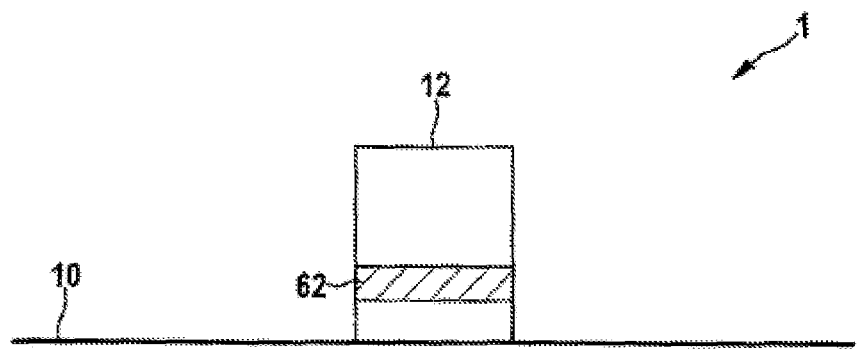
FIG. 6 shows an arrangement according to one embodiment of the present disclosure.
Figure 6:
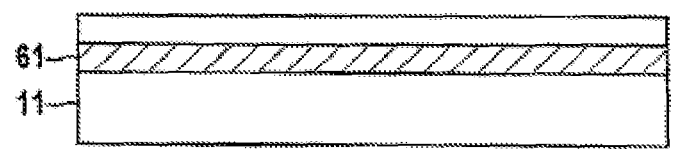

FIG. 6 shows an arrangement 1 according to one embodiment of the present disclosure. The arrangement 1 in FIG. 6 corresponds to the arrangement 1 in FIG. 1, with the exception that the device 11 has an element 61 which aligns the device 11, with which the device 11 can be aligned noninvasively under the skin surface 10. The device 11 can generally be configured as illustrated in the present application.

The element 61 aligning the device 11 can, for example, be a ferromagnetic element. It may be, for example, a plate under the transparent material 53, a ring surrounding the device 11, or a type of "trough" enclosing the transparent material 53 on all sides (except for the side facing the skin surface 10). With the application of a magnetic field (for example using electromagnets or permanent magnets on the light-detecting device 12), a force can be exerted on the device 11 in a non-invasive manner for pulling the device 11 in the direction of the light-detecting device 12 located on the skin surface 10 and/or aligning it with respect to the light-detecting device 12. If the ferromagnetic element 61 itself has a permanent magnetic moment, it is also possible to impart torque in a non-invasive manner.

According to one embodiment of the present disclosure, unique positioning of the device 11 with respect to the light-detecting device 12 can be assured by noninvasively transferring forces and/or torques using the aligning element 61.

According to one embodiment of the present disclosure, the device 11 can be pulled toward the light-detecting device 12 using the aligning element 61, as a result of which the tissue located between the two devices 11, 12 is compromised and as a result of which the portion of blood and tissue fluid in the tissue located therebetween is reduced. By periodically attracting and releasing the device 11 to and from the light-detecting device 12, the tissue located therebetween can be measured alternately with various fluid portions. This is useful in particular for separating influences of tissue and fluids on the absorption spectrum.

According to one embodiment of the present disclosure, the device 11 can be vibrated (briefly) using the aligning element 61 before the optical measurement. As a result, local diffusion processes can be accelerated and chemical gradients in the direct neighborhood of the device 11 can be homogenized. Periodically attracting and repelling the device 11 with respect to the light-detecting device 12 arranged on the skin surface 10 flushes the tissue located therebetween by periodically "flooding" and "squeezing" the fluids in the tissue.

According to FIG. 6, the light-detecting device 12 has an aligning element 62 which is configured to noninvasively align the device 11 under the skin surface such that a side of the light-detecting device 12 which emits the light and receives the fluorescent light is substantially above the side of the device 11 which absorbs the light and emits the fluorescent light.

The present disclosure also permits further embodiments in which the layers, regions of the device 11, which are responsible for collecting the irradiated light 13 and for emitting the fluorescent light 14, are geometrically separated. In this way, spatial separation of the two light intensities is achieved such that for a corresponding configuration of the light-detecting device 12, no light 14' scattered back in another way by the tissue can enter the light-detecting device 12 or be received by the light-detecting device 12.

Figure 7:
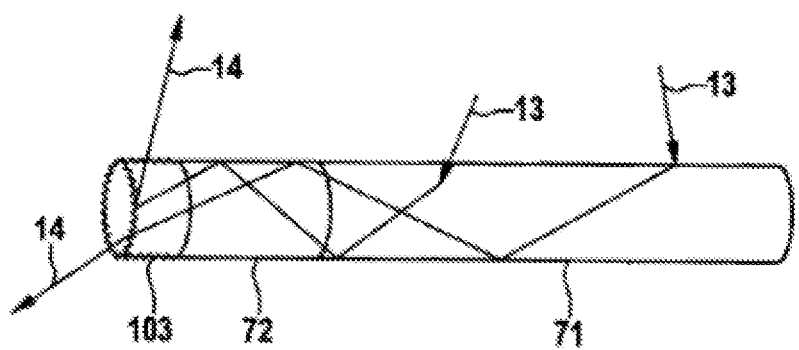
FIG. 7 shows a configuration of the device according to one embodiment of the present disclosure that is insertable under the skin surface.

FIG. 7 shows a configuration of the device 11 which is insertable under the skin surface according to one embodiment of the present disclosure. The device 11 and thus also its substrate 111 consist, according to the present embodiment, of an optical fiber (or of another optical waveguide), one portion 71 of which is provided with a fluorescent layer 112 and which collects the light 13 radiating through the skin surface 10 using the fluorescent layer 112. Alternatively, the portion 71 can also be dyed homogeneously with the fluorescent agent, and one layer may be dispensed with.

According to the present embodiment, the fluorescent portion 71 connects to a further portion 72 without the fluorescent layer 112, wherein in this embodiment the further portion 72 is optional. At the end of the fiber 11, the fluorescent light 14 exits. This end can be regarded as the above-described fluorescent-light-emitting region 113. According to the present embodiment, the end piece or the fluorescent-light-emitting region 113 has a rough surface so as to emit the fluorescent light 14 away from the fiber axis (in the direction of the skin surface 10 and in the direction of the light-detecting device 12) in an amplified manner. This embodiment of the device 11 can be used well for example in a weakly scattering tissue, since the device configured according to the present embodiment makes it possible to increase the portion of ballistic photons at the skin surface 10 which reach the skin surface 10 without scattering in a straight line through the tissue. The higher concentration of the emitted fluorescent light 14 is a result of a considerably greater length of the fiber part 71 which has the fluorescent layer 112 and collects light with respect to the coupling-out end piece 113.

The above-explained embodiments with the specific aspects explained there can be combined with one another. The present disclosure makes possible diverse combinations of the above-described layers of the light source 11 according to the disclosure. Said combinations were not listed in their entirety owing to their large number and for the purposes of precise illustration of the present disclosure, but are clear to the person skilled in the art in view of the description. With the aid of the present disclosure, as it is described, an implantable fluorescent concentrator is inserted in vivo as a subcutaneous light source for optical absorption spectroscopy of surface-near tissue layers. As a result, certain and reliable results of the optical absorption spectroscopy can be achieved. Furthermore, various analytes with different absorption properties can be quantified certainly and reliably. The present disclosure relates to the device configured as a light source, a light-detecting device which detects the light emitted by the light source for the purposes of optical absorption spectroscopy, and an arrangement having the device configured as a light source and the light-detecting device.

What is claimed is:

1. A device configured to be inserted into tissue under a skin surface, comprising:
    a substrate including a material having a higher refractive index than the tissue;
    a fluorescent material supported by the substrate, the fluorescent material configured to absorb light that is emitted onto the skin surface and further configured to convert the absorbed light into fluorescent light and emit the fluorescent light into the substrate such that the fluorescent light is totally internally reflected within the substrate when the device is in the tissue; and
    a fluorescent-light-emitting region supported by the substrate configured to collect the totally internally reflected fluorescent light and further configured to emit the collected fluorescent light in a direction of the skin surface to leave the tissue.

2. The device according to claim 1, wherein the fluorescent material is formed on the substrate of the device.

3. The device according to claim 1, wherein the fluorescent-light-emitting region is smaller than a side of the device configured to face the skin surface.

4. The device according to claim 1, wherein:
    the fluorescent-light-emitting region is one of a roughened region and a region covered with scattering particles, and
    the device further comprises a reflector at a side of the fluorescent-light-emitting region configured to face away from the skin surface.

5. The device according to claim 1, further comprising at least one mirror arranged at least at one front end of the device, the at least one mirror configured to reflect into the device light rays of the fluorescent light which radiate into the device and against the front end of the device.

6. The device according to claim 1, further comprising:
    a fluorescent-light-controlling layer on a side of the device configured to face the skin surface,
    wherein the fluorescent-light-controlling layer is formed above the fluorescent material,
    wherein the fluorescent-light-controlling layer is substantially transparent for the light emitted onto the skin surface,
    wherein the fluorescent-light-controlling layer is substantially reflective or absorbing for the fluorescent light, and
    wherein the fluorescent-light-controlling layer is configured to direct the emission of the collected fluorescent light to a specific position on the skin surface.

7. The device according to claim 6, wherein the fluorescent-light-controlling layer is open with respect to the fluorescent-light-emitting region such that the fluorescent light emitted by the fluorescent-light-emitting region is emitted to a specific position on the skin surface.

8. The device according to claim 1, further comprising an element configured to align the device, the element further configured to enable the device to be aligned noninvasively under the skin surface.

9. The device according to claim 1, wherein the fluorescent material includes a fluorescent dye.

10. The device according to claim 1, wherein the fluorescent material includes the material of the substrate and a fluorescent dye.

11. The device according to claim 1, wherein:
    the fluorescent-light-emitting region is a surface of the substrate that extends with the skin surface, and
    the fluorescent-light-emitting region is one of a roughened region and a region covered with scattering particles.

12. The device according to claim 1, wherein the fluorescent-light-emitting region is a light-scattering region in a volume of the substrate.

13. An arrangement, comprising:
    a device configured to be inserted into tissue under a skin surface, the device including:
        a substrate including a material having a higher refractive index than the tissue;

a fluorescent material supported by the substrate, the fluorescent material configured to absorb light that is emitted onto the skin surface and further configured to convert the absorbed light into fluorescent light and emit the fluorescent light into the substrate such that the fluorescent light is totally internally reflected within the substrate when the device is in the tissue; and a fluorescent-light-emitting region supported by the substrate configured to collect the totally internally reflected fluorescent light and further configured to emit the collected fluorescent light in a direction of the skin surface; and a light-detecting device configured to emit light onto the skin surface and further configured to detect and receive the fluorescent light emitted by the device.

14. The arrangement according to claim 13, wherein the light-detecting device includes a filter element configured to transmit the fluorescent light for evaluation in the light-detecting device and further configured to block other light emitted by the skin surface.

15. The arrangement according to claim 13, further comprising an aligning element configured to noninvasively align the device under the skin surface such that a side of the light-detecting device which is configured to emit the light and to receive the fluorescent light is substantially above a side of the device which absorbs the light and emits the fluorescent light.

* * * * *